United States Patent [19]

Stoltefuss et al.

[11] Patent Number: 4,772,611

[45] Date of Patent: Sep. 20, 1988

[54] CIRCULATION-ACTIVE 3-AMINO-DIHYDROPYRIDINES

[75] Inventors: Jürgen Stoltefuss, Haan; Fred R. Heiker, Wuppertal; Martin Bechem, Wuppertal; Rainer Gross, Wuppertal; Michael Kayser, Hagen; Matthias Schramm, Cologne, all of Fed. Rep. of Germany; Günter Thomas, Garbagnate, Italy

[73] Assignee: Bayer Aktiengesellschaft, Leverkusen, Fed. Rep. of Germany

[21] Appl. No.: 43,656

[22] Filed: Apr. 28, 1987

[30] Foreign Application Priority Data

May 7, 1986 [DE] Fed. Rep. of Germany ....... 3615404

[51] Int. Cl.$^4$ .................. A61K 31/455; C07D 211/90; C07D 491/048
[52] U.S. Cl. .................... 514/302; 514/352; 546/116; 546/310; 546/311
[58] Field of Search .............. 546/310, 311, 116; 514/352, 302

[56] References Cited

U.S. PATENT DOCUMENTS 4,532,248  7/1985  Franckowiak et al. ............. 514/302

Primary Examiner—Mary C. Lee
Assistant Examiner—Dale A. Bjorkman
Attorney, Agent, or Firm—Sprung Horn Kramer & Woods

[57] ABSTRACT

Novel cardioactive compounds of the formula

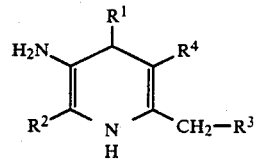

in which
$R^1$ is alkyl, aryl or heterocyclic, preferably substituted phenyl,
$R^2$ is alkyl, preferably methyl,
$R^3$ is hydrogen, halogen, acyloxy or alkyl, preferably hydrogen, and
$R^4$ is phenyl, carbalkoxy or together with $R^3$ forms a ring, preferably carbalkoxy, are produced by reducing the corresponding nitro compounds.

9 Claims, No Drawings

CIRCULATION-ACTIVE 3-AMINO-DIHYDROPYRIDINES

The invention relates to 3-amino-dihydropyridines a process for their preparation, and their use in medicaments, in particular in medicaments affecting the circulation.

The invention relates to 3-amino-dihydropyridines of the general formula (I)

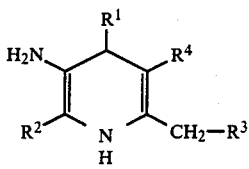

in which
R$^1$ represents straight-chain, branched or cyclic alkyl which has up to 8 carbon atoms and is optionally substituted by phenyl, pyridyl or pyrimidyl, or represents a heterocyclic radical from the series comprising thienyl, furyl, pyridyl, pyrimidyl, quinolyl, benzoxadiazolyl, benzoxazolyl, benzothiazolyl or isoquinolyl, or represents phenyl which is optionally substituted up to four times, identically or differently, by C$_1$-C$_6$ alkyl, C$_1$-C$_6$-alkoxy, C$_1$-C$_6$-alkylthio, carboxyl, carboxy-C$_1$-C$_4$-alkyl, dioxyethylene, dioxymethylene, halogen, cyano, trifluoromethyl, trifluoromethoxy, difluoromethoxy, trifluoromethylthio, phenylsulphonyl, phenylsulphonyloxy, C$_1$-C$_4$-alkylsulphonyl or by a group of the formula

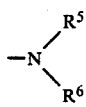

in which
R$^5$ and R$^6$ are identical or different and represent hydrogen, C$_1$-C$_6$-alkyl, phenyl, benzyl, acetyl, benzoyl, phenylsulphonyl, tolylsulphonyl or C$_1$-C$_6$-alkylsulphonyl,
R$^2$ represents straight-chain or branched alkyl which has up to 6 carbon atoms and is optionally substituted by hydroxyl, phenyl or halogen, or represents phenyl,
R$^3$ represents hydrogen or represents halogen or C$_2$-C$_7$-acyloxy or represents straight-chain or branched alkyl having up to 4 carbon atoms, and
R$^4$ represents phenyl or represents a group of the formula —CO$_2$R$^7$,
in which
R$^7$ represents straight-chain or branched alkyl which has up to 10 carbon atoms and is optionally interrupted in the chain by an oxygen atom and/or is optionally substituted by halogen, cyano, hydroxyl or acetyloxy, or by a phenyl, phenylsulphonyl or phenoxy group each of which is optionally substituted by halogen, cyano, C$_1$-C$_4$-alkyl, C$_1$-C$_4$-alkoxy or trifluoromethyl, or by an α-, β-, or γ-pyridyl group, or by an amino group, it being possible for this amino group to carry two identical or different substituents from the series comprising C$_1$-C$_4$-alkyl, phenyl or benzyl, or R$^7$ and R$^3$ together represent a bond,
and to their physiologically acceptable salts.

Preferred compounds are those of the general formula (I) in which
R$^1$ represents straight-chain, branched or cyclic alkyl having up to 6 carbon atoms, or represents pyridyl, thienyl, benzoxadiazolyl or pyrimidyl, or represents phenyl which is optionally substituted up to 3 times, identically or differently, by C$_1$-C$_4$-alkyl, C$_1$-C$_4$-alkoxy, fluorine chlorine, bromine, carboxyl, cyano, trifluoromethyl, trifluoromethoxy or trifluoromethylthio, or by a group of the formula

in which
R$^5$ and R$^6$ are identical or different and represent hydrogen, C$_1$-C$_4$-alkyl, phenyl, benzyl, acetyl or benzoyl,
R$^2$ represents straight-chain or branched alkyl having up to 4 carbon atoms,
R$^3$ represents hydrogen, fluorine, chlorine, bromine, iodine, acetyloxy or benzoyloxy, or represents methyl, and
R$^4$ represents phenyl or represents a group of the formula —CO$_2$R7,
R$^7$ represents straight-chain or branched alkyl which has up to 8 carbon atoms, is optionally interrupted in the chain by an oxygen atom and/or is optionally substituted by up to 7 fluorine atoms, by chlorine, bromine, cyano, hydroxyl, acetyloxy, phenyl, phenoxy, α-, β- or γ-pyridyl or by an amino group, it being possible for this amino group to carry two identical or different substituents from the group comprising C$_1$-C$_2$alkyl or benzyl, or
R$^7$ and R$^3$ together represent a bond,
and their physiologically acceptable salts.

Particularly preferred compounds are those of the general formula (1) in which
R$^1$ represents straight-chain or branched alkyl
having up to 4 carbon atoms, or represents phenyl which is optionally substituted up to three times, identically or differently, by C$_1$-C$_4$-alkyl, C$_1$-C$_4$-alkoxy, chlorine, cyano, trifluoromethyl, trifluoromethoxy or trifluoromethylthio,
R$^2$ represents methyl,
R$^3$ represents hydrogen, chlorine, bromine, acetyloxy, benzoyloxy or methyl, and
R$^4$ represents phenyl or represents the group of the formula —CO$_2$R$^7$,
in which
R$^7$ represents straight-chain or branched alkyl which has up to 6 carbon atoms, is optionally interrupted in the chain by an oxygen atom and/or is optionally substituted by up to 3 fluorine, by chlorine, cyano, hydroxyl, acetyl or N-benzyl-N-methylamino or
R$^7$ and R$^3$ together represents a bond,
and their physiologically acceptable salts.

Possible physiologically acceptable salts are salts of the free bases with inorganic or organic acids. Preference is given to salts with inorganic acids, such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid or methanesulphonic acid, ethanesulphonic acid, phenylsulphonic acid, toluenesulphonic acid or naphthalenedisulphonic acid.

The compounds according to the invention exist in stereoisomeric forms which either are related as image and mirror image (enantiomers) or are not related as image and mirror image (diastereomers). The invention relates to both the antipodes and the racemic forms as well as mixtures of diastereomers. The racemic forms can, as can the mixtures of diastereomers, be separated into the stereoisomerically homogeneous constituents in a known manner (compare E. L. Eliel, Stereochemistry of Carbon Compounds, McGraw Hill, 1962).

The compounds according to the invention, of the general formula (I), are obtained when 3-nitro-dihydropyridines of the general formula (II)

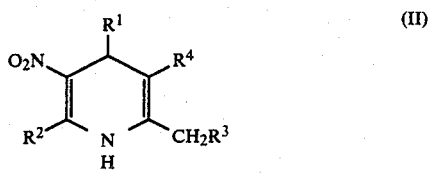

in which $R^1-R^4$ have the indicated meaning, are reduced in the presence of a catalyst, in the presence of an acid and, where appropriate, in the presence of an inert solvent, and, where appropriate, the free amino compounds are prepared from the salts with bases.

When methyl 1,4-dihydro-2,6-dimethyl-3-nitro-4-(3-trifluoromethylphenyl)pyridine-5-carboxylate is used as starting material, the preparation of the compounds according to the invention can be illustrated by the following diagram:

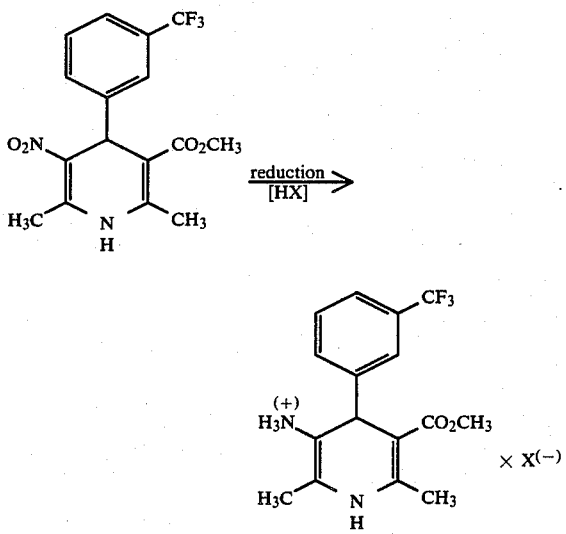

The 3-nitro-dihydropyridines used as starting materials are known or can be prepared by known methods (Belgian Patent Specification No. 893984).

The reduction is carried out, in general, by hydrogenation using metal catalysts such as, for example, platinum, palladium, palladium on animal charcoal, $PtO_2$ or Raney nickel, preferably using palladium on animal charcoal, in the presence of acids.

The acids which can be used according to the invention are strong mineral acids as well as organic acids. These are preferably hydrochloric acid, hydrobromic acid, sulphuric acid, phosphoric acid or carboxylic acids such as acetic acid, oxalic acid or trifluoroacetic acid, or sulphonic acids such as methane-, ethane-, phenyl- or toluenesulphonic acid or naphthalenedisulphonic acid.

The catalyst is used for this, in general, in an amount of 0.1 to 50 mol-%, preferably of 1 to 10 mol-% relative to 1 mol of the nitrodihydropyridine.

The hydrogenation is carried out, in general, in the temperature range from $-20°$ C., to $+100°$ C., preferably in the range from $0°$ C. to $50°$ C.

In general, the hydrogenation is carried out with an excess pressure from 2 to 200 bar, preferably from 2 to 50 bar.

It is equally possible to carry out the hydrogenation under atmospheric pressure.

Suitable solvents for the hydrogenation are water and/or inert organic solvents. These preferably include alcohols such as, for example, methanol, ethanol, propanol or isopropanol, ethers such as diethyl ether, dioxane, tetrahydrofuran, glycol monomethyl or dimethyl ether, chlorinated hydrocarbons such as methylene chloride, chloroform or carbon tetrachloride, glacial acetic acid, trifluoroacetic acid, dimethylformamide and ethyl acetate. It is equally possible to use mixtures of the said solvents.

The reduction is particularly preferably carried out with noble metal catalysts in alcohols in the presence of acid under an excess pressure of hydrogen.

The yield of the compounds prepared according to the invention depends on the choice of the catalyst, the acid and the hydrogenation conditions (pressure and dura- tion).

The free amino compounds are obtained by reaction of the salts according to the invention with bases. The bases which can be used are the usual basic compounds for basic reactions. These preferably include ammonia or alkali metal and alkaline earth metal hydroxides or carbonates such as, for example, lithium hydroxide, sodium hydroxide, potassium hydroxide, calcium or barium hydroxide, sodium or potassium Carbonale, alkali melal alcoholates such as, for example, sodium methanolate and ethanolate, or potassium methanolate or ethanolate, or organic bases such as, for example, triethylamine, pyridine or 1-methylpiperidine, benzyltrimethylammonium hydroxyide or tetrabutylammonium hydroxide.

The compounds according to the invention show a valuable spectrum of pharmacological action which could not have been foreseen. They affect the contractility of the heart and the tone of smooth muscle. Hence they can be used in medicaments for influencing pathologically altered blood pressure, and coronary therapeutics and for the treatment of cardiac insufficiency. Furthermore, they can be used for the treatment of cardiac arrhythmias, for lowering blood sugar, to reduce mucosal swelling and to influence the salt and fluid balance.

The cardiac actions were found on isolated, perfused hearts from albino guinea-pigs weighing 200 g and of both sexes, the hearts being perfused with suitable dilutions of the substances. For this purpose, the animals were sacrificed, the thorax was opened, a metal cannula was tied into the exposed aorta, and the left atrium was opened.

The heart and lungs were dissected out of the thorax and connected, via the cannula in the aorta, to the perfusion apparatus with perfusion in progress. The lungs were cut off at the roots of the lungs. The perfusion medium used was a Krebs-Henseleit solution (118 mmol/l NNaCl, 4.8 mmol/l KCl, 1.2 mmol MgSO4, 119 mmol/l NaEDTA, pH 7.4, 10 mmol/l glucose) containing 1.2 mmol/l CaCl2 which had been filtered to remove particles before the perfusion. The hearts were perfused with a constant flow rate of 10 ml/min at 32° C. The contractions of the heart were measured isovolumetrically using a latex balloon introduced into the left ventricle and were recorded on a high-speed pen recorder.

The actions on the contractility of some examples of the compounds according to the invention are listed in Table 1.

TABLE 1

At a concentration of $10^{-6}$ g/ml substance, the percentage increase in the left-ventricular isovolumetric amplitude of contraction, compared with the initial figure which is set equal to 100% is for

| | |
|---|---|
| Example No. 3 | +32% |
| Example No. 4 | +33% |
| Example No. 5 | +23% |
| Example No. 8 | +12% |

The new active compounds can be converted in a known manner into the customary formulations, such as tablets, coated tablets, pills, granules, aerosols, syrups, emulsions, suspensions and solutions, using inert, non-toxic, pharmaceutically suitable vehicles or solvents. The therapeutically active compound should in each case be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example, when using water as a diluent, organic solvents can optionally be used as auxiliary solvents.

Examples of auxiliaries which may be mentioned are: water, non-toxic organic solvents, such as paraffins (for examole petroleum fractions), vegetable oils (for example groundnut oil/sesame oil), alcohols (for example ethyl alcohol and glycerol), solid vehicles, such as, for example, natural rock powders (for example kaolins, aluminas, talc and chalk), synthetic rock powders (for example highly disperse silica and silicates) and sugars (for example sucrose, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose starch and polyvinylpyrrolidonel and lubricants for example magnesium stearate, talc, stearic acid and sodium laurylsulphate).

Administration is effected in the customary manner, preferably orally or parenterally, in particular perlingually or intravenously. In the case of oral administration, the tablets can, of course, also contain in addition to the vehicles mentioned, additives such as sodium citrate, calcium carbonate and dicalcium phosphate, together with various additional substances, such as starch, preferably potato starch, gelatine and the like. Furthermore, lubricants such as magnesium stearate, sodium lauryl sulphate and talc can also be used when making tablets.

In the case of aqueous suspensions various taste improvers or dyestuffs can be added to the active compounds in addition to the abovementioned auxiliaries.

In the case of parenteral administration solutions of the active compounds can be employed using suitable liquid carrier materials.

In general it has proven advantageous for the achievement of effective results to administer quantities of about 0.001 to 1 mg/kg, preferably about 0.01 to 0.5 mg/kg body weight in the case of intravenous administration and in the case of oral administration the dosage is about 0.01 to 20 mg/kg, preferably 0 1 to 10 mg/kg body weight.

Nevertheless, it can at times be necessary to deviate from the amounts mentioned, and in particular to do so as a function of the body weight of the experimental animal or of the nature of the administration method, but also because of the species of animal and its individual behavior towards the medicament, or the nature of the formulation of the medicament and the time or interval over which the administration takes place. Thus it can suffice in some cases to manage with less than the abovementioned minimum amount, while in other cases the upper limit mentioned must be exceeded. Where relatively large amounts are administered, it can be advisable to divide these into several individual administrations over the course of the day. The same dosage range is envisaged for administration in human medicine. In this connection the above statements similarly apply.

EXAMPLE 1

Methyl 3-amino-1,4-dihydro-2,6-dimethyl-4-(3-methylphenyl) pyridine 5-carboxylate hydrochloride

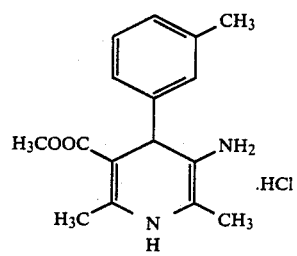

2 g (6.63 mmol) of methyl 1,4-dihydro-2,6-dimethyl4-(3-methylphenyl)-3-nitro-pyridine-5-carboxylate are dissolved in 80 ml of methanol, and 1.53 ml (13.2 mmol) of 8.6 molar HCl in methanol and 200 mg of 10% palladium on active charcoal are added, and hydrogenation is carried out under 3.5 bar until the yellow color of the solution has disappeared. The reaction was complete after 17 minutes. The mixture is filtered and concentrated. The oily residue from evaporation is dissolved in acetonitrile and concentrated again, crystallization occurring. The crystals are washed with acetonitrile. 1.3 g (63.7% of theory) of colorless crystals of melting point 180°-182° C., with decomposition, are obtained.

EXAMPLE 2

Methyl
3-amino-1,4-dihydro-2,6-dimethyl-4-(3-methylphenyl)-
pyridine-5-carboxylate
semi-naphthalene-1,5-disulphonate

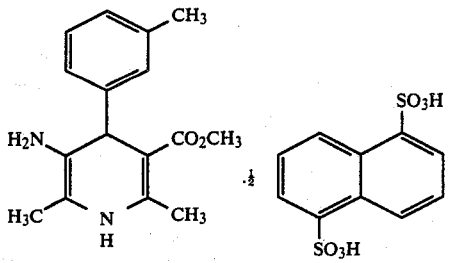

1 g (3.31 mmol) of methyl 1,4-dihydro-2,6-dimethyl-4-(3-methylphenyl)-3-nitro-pyridine-5-carboxylate is dissolved in 40 ml of methanol, and 923 mg (3.31 mmol) of naphthalene-1,5-disulphonic acid and 100 mg of 10% Pd/C are added. Hydrogenation is carried out under atmospheric pressure until the reaction is complete after 1.5 hours. The mixture is filtered, concentrated, acetone is added, and concentration is repeated. The semisolid product is stirred with acetone and with a little methanol, filtered off with suction, and washed with acetone. 0.5 g of colorless crystals of melting point 223° C., with decomposition, is obtained.

The following are prepared in analogy to Example 1:

EXAMPLE 3

Isopropyl    3-amino-1,4-dihydro-2,6-dimethyl-4-(3-methylphenyl)-pyridine-5-carboxylate    hydrochloride of melting point 187° C. with decomposition.

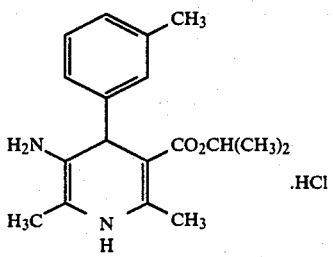

EXAMPLE 4

Methyl   3-amino-1,4-dihydro-2,6-dimethyl-4-(2-trifluoromethylphenyl) -pyridine-5-carboxylate hydrochloride of melting point 180°-182° C. with decomposition.

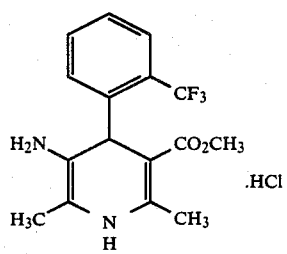

EXAMPLE 5

Isopropyl    3-amino-1,4-dihydro-2,6-dimethyl-4-(2-chlorophenyl)-pyridne-5-carboxylate hydrochloride of melting point 164°-166° C. with decomposition.

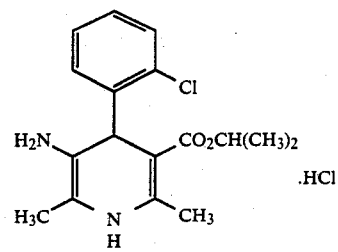

EXAMPLE 6

Methyl    3-amino-1,4-dihydro-2,6-dimethyl-4-isopropylpyridine-5-carboxylate hydrochloride of melting point 159°-162° C. with decomposition.

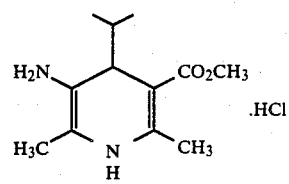

EXAMPLE 7

μ-Hydroxyethyl
3-amino-1,4-dihydro-2,6-dimethyl-4-(3chlorophenyl)-
pyridine-5-carboxylate hydrochloride $R_f$ 0.025

TLC: silica gel 60 F 254 aluminium roll, Merck

Mobile phase: toluene/ethyl acetate in the ratio by volume 1:1

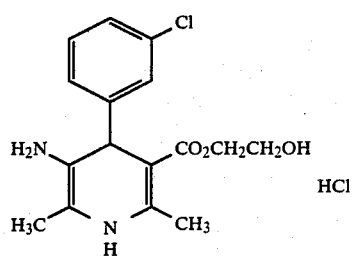

EXAMPLE 8

Isopropyl    3-amino-1,4-dihydro-2,6-dimethyl-4-(2-methylphenyl)-pyridine-5-carboxylate    hydrochloride of melting point 151°-56° C. with decomposition.

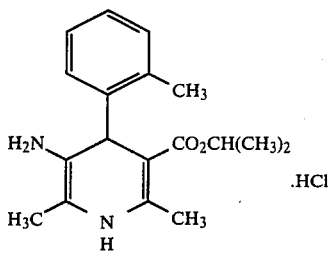

EXAMPLE 9

3-Amino-1,4-dihydro-2,6-dimethyl-4-(4-trifluoromethylmercaptophenyl)-5-phenyl-pyridine hydrochloride $R_f$ 0.225

TLC: Silica gel 60 F 254 aluminium roll, Merck Mobile phase: toluene/ethyl acetate in the ratio by volume 1:1

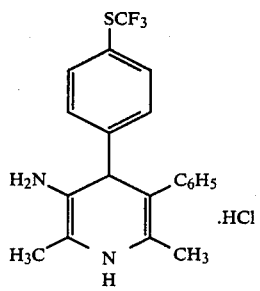

The following are prepared in analogy to Example 2:

EXAMPLE 10

3-Amino-2-methyl-4-(3-methylphenyl)-5-oxo-1,4,5,7-tetrahydrofuro [3,4-b]pyridineseminaphthalene-1,5-disulphonate of melting point above 260° C. with decomposition.

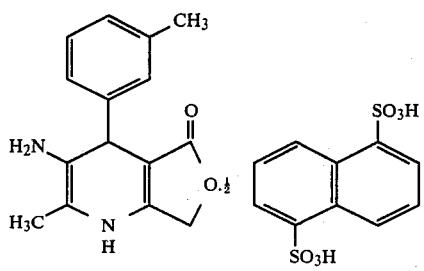

EXAMPLE 11

Methyl 3-amino-1,4-dihydro 2,6-dimethyl-4-(2-trifluoromethylphenyl)-pyridine-5-carboxylate

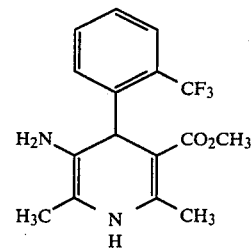

0.5 g of compound from Example 4 is stirred with 10 ml of water under argon, and the mixture is made alkaline by addition of 5 ml of ammonia with stirring, this resulting in the pale yellow free base. Under argon, it is filtered off with suction, washed with water and dried. 340 mg of a pale yellow substance are obtained. Melting point: beginning at 70° C. with decomposition.

It is understood that the specification and examples are illustrative but not limitative of the present invention and that other embodiments within the spirit and scope of the invention will suggest themselves to those skilled in the art.

We claim:

1. A 3-amino-dihydropyridine of the formula

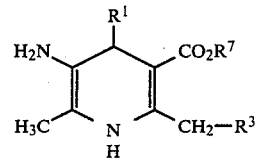

in which $R^1$ phenyl which is optionally substituted up to three times, identically or differently, by $C_1$-$C_4$-alkyl, $C_1$-$C_4$-alkoxy, chlorine, cyano, trifluoromethyl, trifluoromethoxy or trifluoromethylthio, $R^3$ represents hydrogen, chlorine, bromine, acetyloxy, benzoyloxy or methyl, and $R^7$ represents straight-chain or branched alkyl which has up to 6 carbon atoms, is optionally interrupted in the chain by an oxygen atom and/or is optionally substituted by up to 3 fluorine, by chlorine, cyano, hydroxyl, acetyl or N-benzyl-N-methylamino or $R^7$ and $R^3$ together represent a bond, or a physiologically acceptable salt thereof.

2. A compound according to claim 1, wherein such compound is isopropyl 3-amino-1,4-dihydro-2,6-dimethyl-4-(3-methylphenyl)-pyridine-5-carboxylate of the formula

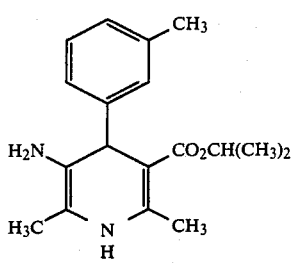

or a physiologically acceptable salt thereof.

3. A compound according to claim 1, wherein such compound is methyl 3-amino-1,4-dihydro-2,6-dimethyl-4-(2-trifluoromethylphenyl)-pyridine-5-carboxylate of of the formula

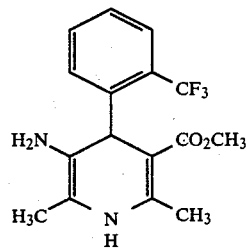

or a physiologically acceptable salt thereof.

4. A compound according to claim 1, wherein such compound is isopropyl 3-amino-1,4-dihydro-2,6-dimethyl-4-(2-chlorophenyl) -pyridine-5-carboxylate of the formula

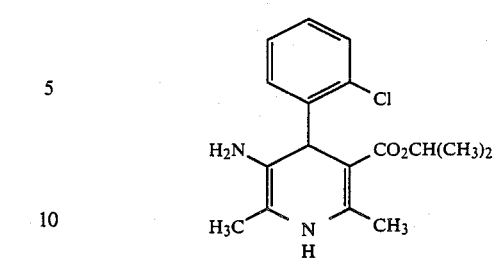

or a physiologically acceptable salt thereof.

5. A compound according to claim 1, wherein such compound is isopropyl 3-amino-1,4-dihydro-2,6-dimethyl 4-(2-methylphenyl)-pyridine-5-carboxylate of the formula

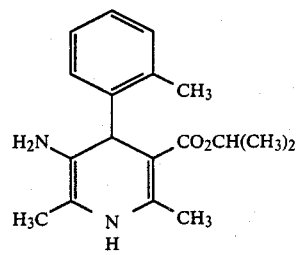

or a physiologically acceptable salt thereof.

6. A cardioactive composition for increasing the contractility of the heart comprising an amount effective thereof of a compound or salt according to claim 1 and a diluent.

7. A unit dose of a composition according to claim 6 in the form of a tablet, capsule or ampule.

8. A method of increasing the contractility of the heart in a patient in need thereof which comprises administering to a patient in need thereof an amount effective therefor of a compound or salt according to claim 1.

9. The method according to claim 8, wherein such compound is
isopropyl 3-amino-1,4-dihydro-2,6-dimethyl-4-(3-methylphyenyl)-pyridine-5-carboxylate,
methyl 3-amino-1,4-dihydro-2,6-dimethyl-4-(2-trifluoromethylphenyl) -pyridine-5carboxylate,
isopropyl 3-amino-1,4-dihydro-2,6-dimethyl-4-(2-chlorophenyl)-pyridine-5-carboxylate or
isopropyl 3-amino-1,4-dihydro-2,6-dimethyl-4(2-methylphenyl-pyridine-5-carboxylate,
or a physiologically acceptable salt thereof.

* * * * *

UNITED STATES PATENT AND TRADEMARK OFFICE
CERTIFICATE OF CORRECTION

PATENT NO. : 4,772,611

DATED : September 20, 1988

INVENTOR(S) : Jürgen Stoltefuss, et al

It is certified that error appears in the above-identified patent and that said Letters Patent is hereby corrected as shown below:

| | |
|---|---|
| Col. 2, lines 9 and 10 | Delete "c4" and substitute --$C_4$-- |
| Col. 2, line 10 | After "fluorine" insert --,-- |
| Col. 2, line 30 | Delete "-$CO_2R7$" and substitute --$CO_2R^7$, in which-- |
| Col. 2, line 39 | After "$C_1-C_2$" insert -- - -- |
| Col. 4, line 36 | Delete "dura- tion" and substitute --duration-- |
| Col. 4, line 44 | Delete "Carbonale," and substitute --carbonate,-- |
| Col. 4, line 45 | Delete "melal" and substitute --metal-- |
| Col. 5, line 7 | After "mmol/l"(first instance) insert --$Mg\ SO_4$, 25 mmol/l $NaHCO_3$, 0.013 mmol/l-- |
| Col. 5, line 45 | Delete "examole" and substitute --example-- |
| Col. 5, line 56 | Delete "polyvinylpyrrolidonel" and substitute --polyvinylpyrrolidone)-- |
| Col. 5, line 56 | Before "for example" insert --(-- |
| Col. 6, line 14 | Delete "0 1" and substitute --0.1-- |
| Col. 8, line 2 | Correct --pyridine-- |
| Col. 8, line 40 | Delete "µ-Hydroxyethyl" and substitute --β-Hydroxyethyl-- |
| Col. 8, line 41 | After "3" and before "chlorophenyl" insert -- - -- |

UNITED STATES PATENT AND TRADEMARK OFFICE
CERTIFICATE OF CORRECTION

PATENT NO. : 4,772,611

DATED : September 20, 1988

INVENTOR(S) : Jürgen Stoltefuss, et al

It is certified that error appears in the above-identified patent and that said Letters Patent is hereby corrected as shown below:

Col. 12, line 47      After "5" and before "carboxylate" insert -- - --

Col. 12, line 50      After "4" and before "(2-" insert -- - --

Signed and Sealed this

Sixteenth Day of May, 1989

Attest:

DONALD J. QUIGG

Attesting Officer     Commissioner of Patents and Trademarks